United States Patent [19]

Bach et al.

[11] Patent Number: 5,919,774
[45] Date of Patent: Jul. 6, 1999

[54] PYRROLES AS SPLA$_2$ INHIBITORS

[75] Inventors: Nicholas J. Bach, Indianapolis; Robert D. Dillard, Zionsville; Susan E. Draheim, Indianapolis, all of Ind.

[73] Assignee: Eli Lilly and Company, Indianapolis, Ind.

[21] Appl. No.: 08/985,518

[22] Filed: Dec. 5, 1997

Related U.S. Application Data

[60] Provisional application No. 60/033,290, Dec. 10, 1996.
[51] Int. Cl.$^6$ .................... A61K 31/40; C07D 207/323; C07D 207/36; C07F 9/572
[52] U.S. Cl. ............................ 514/91; 514/423; 514/424; 514/427; 548/413; 548/530; 548/539; 548/540; 548/550; 548/561
[58] Field of Search ..................................... 548/413, 530, 548/539, 540, 561, 550; 514/423, 427, 424, 91

[56] References Cited

U.S. PATENT DOCUMENTS

| 4,132,788 | 1/1979 | Wong | 424/232 |
| 4,870,076 | 9/1989 | Heckel et al. | 514/252 |
| 5,187,168 | 2/1993 | Primeau et al. | 514/259 |
| 5,260,322 | 11/1993 | Nakasima et al. | 514/341 |

FOREIGN PATENT DOCUMENTS 300 688  1/1989  European Pat. Off. .

OTHER PUBLICATIONS

Kim, et al., Tetrahedron Letters, 1994, 35(19), 3017.
Pataki, et al., J. Org. Chem., 1982, 47,1133.
Reetz, et al., J. Org. Chem., 1983, 48, 254.

*Primary Examiner*—Mukund J. Shah
*Assistant Examiner*—Ann M. Kessinger
*Attorney, Agent, or Firm*—Arleen Palmberg

[57] ABSTRACT

A class of novel pyrroles is disclosed together with the use of such compounds for inhibiting sPLA$_2$ mediated release of fatty acids for treatment of conditions such as septic shock.

10 Claims, No Drawings

PYRROLES AS SPLA₂ INHIBITORS

This application claims the benefit of U.S. Provisional Application Ser. No. 60/033,290, filed Dec. 10, 1996.

BACKGROUND OF THE INVENTION

This invention relates to novel substituted pyrroles useful for inhibiting sPLA$_2$ mediated release of fatty acids for conditions such as septic shock.

BACKGROUND INFORMATION

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of Apr. 5, pp. 5335–5338, 1989; and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of Apr. 5, pp. 5768–5775, 1989; the disclosures of which are incorporated herein by reference.

It is believed that sPLA$_2$ is a rate limiting enzyme in the arachidonic acid cascade which hydrolyzes membrane phospholipids. Thus, it is important to develop compounds which inhibit sPLA$_2$ mediated release of fatty acids (e.g., arachidonic acid). Such compounds would be of value in general treatment of conditions induced and/or maintained by overproduction of sPLA$_2$; such as septic shock, adult respiratory distress syndrome, pancreatitis, trauma-induced shock, bronchial asthma, allergic rhinitis, rheumatoid arthritis etc.

It is desirable to develop new compounds and treatments for sPLA$_2$ mediated diseases.

SUMMARY OF THE INVENTION

This invention provides compounds of the formula I

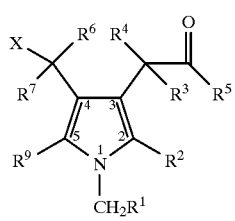

(I)

$R^1$ is hydrogen, —(C$_1$–C$_4$)alkyl, phenyl or phenyl substituted with one or two substituents selected from the group consisting of —(C$_1$–C$_4$)alkyl, (C$_1$–C$_4$)alkoxy, phenyl(C$_1$–C$_4$)alkyl, (C$_1$–C$_4$)alkylthio, halo and phenyl;

$R^2$ is hydrogen, —(C$_1$–C$_4$)alkyl, halo, (C$_1$–C$_4$)alkoxy, or (C$_1$–C$_4$) alkylthio;

$R^3$ and $R^4$ are each hydrogen or when taken together are =O;

$R^5$ is —NH$_2$ or —NHNH$_2$;

$R^6$ and $R^7$ are each hydrogen or when one of $R^6$ and $R^7$ is hydrogen, the other is —(C$_1$–C$_4$)alkyl, —(CH$_2$)$_n$R$^{10}$ where $R^{10}$ is —CO$_2$R$^{11}$, —PO$_3$(R$^{11}$)$_2$, —PO$_4$(R$^{11}$)$_2$ or —SO$_3$R$^{11}$ where $R^{11}$ is independently hydrogen or —(C$_1$–C$_4$)alkyl and n is 1 to 4; or $R^6$ and $R^7$, taken together, are =O or =S;

X is $R^8$(C$_1$–C$_6$)alkyl; $R^8$(C$_2$–C$_6$)alkenyl or phenyl substituted at the ortho position with $R^8$ where $R^8$ is (CH$_2$)$_n$R$^{10}$ where $R^{10}$, $R^{11}$ and n are as defined above, and additionally substituted with one or two substituents selected from the group consisting of hydrogen, —(C$_1$–C$_4$)alkyl, halo, (C$_1$–C$_4$)alkoxy, or two substituents which, when taken together with the phenyl ring to which they are attached, form a naphthyl group; and $R^9$ is hydrogen or —(C$_1$–C$_4$)alkyl;

or a pharmaceutically acceptable salt or optical isomer thereof.

These compounds are effective in inhibiting human sPLA$_2$ mediated release of fatty acids.

This invention is also a pharmaceutical formulation comprising a compound of formula I in association with one or more pharmaceutically acceptable diluents, carriers and excipients.

This invention is also a method of inhibiting sPLA$_2$ comprising administering to a mammal in need of such treatment a therapeutically effective amount of a compound of formula I.

According to a further aspect of the present invention, there is provided a method of selectively inhibiting sPLA$_2$ in a mammal in need of such treatment comprising administering to said mammal a therapeutically effective amount of a compound of formula I.

This invention also provides a method of alleviating the pathological effects of septic shock, adult respiratory distress syndrome, pancreatitis, trauma-induced shock, bronchial asthma, allergic rhinitis, rheumatoid arthritis, and related diseases which comprises administering to a mammal in need of such treatment a therapeutically effective amount of the compound of formula I in an amount sufficient to inhibit sPLA$_2$ mediated release of fatty acid and to thereby inhibit or prevent the arachidonic acid cascade and its deleterious products.

Other objects, features and advantages of the present invention will become apparent from the subsequent description and the appended claims.

DETAILED DESCRIPTION OF THE INVENTION

Definitions:

As used herein, the term, "(C$_1$–C$_6$)alky" by itself or as part of another substituent means, unless otherwise defined, a straight or branched chain monovalent hydrocarbon radical such as methyl, ethyl, n-propyl, isopropyl, n-butyl, tertiary butyl and isobutyl. The term "(C$_1$–C$_6$)alkyl" includes —(C$_1$–C$_4$)alkyl and —(C$_1$–C$_2$)alkyl.

The term "phenyl(C$_1$–C$_4$)alkyl" refers to a straight or branched chain alkyl group having from one to four carbon atoms attached to a phenyl ring which chain is attached to the remainder of the molecule. Typical phenylalkyl groups include benzyl, phenylethyl, phenylpropyl, phenylisopropyl, and phenylbutyl.

The term, "(C$_2$–C$_6$)alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term "halo" means chloro, fluoro, bromo or iodo.

The term "(C$_1$–C$_4$)alkoxy" defines a straight or branched alkyl chain having one to four carbon atoms attached to the remainder of the molecule by an oxygen atom. Typical ($C_1$–$C_4$)alkoxy groups include methoxy, ethoxy, n-propoxy, isopropoxy, n-butoxy, t-butoxy and the like.

The term "($C_1$–$C_4$)alkylthio" defines a straight or branched alkyl chain having one to four carbon atoms attached to the remainder of the molecule by a sulfur atom. Typical ($C_1$–$C_4$)alkylthio groups include methylthio, ethylthio, propylthio, butylthio and the like.

The term "acid protecting group" is used herein as it is frequently used in synthetic organic chemistry, to refer to a group which will prevent an acid group from participating in a reaction carried out on some other functional group of the molecule, but which can be removed when it is desired to do so. Such groups are discussed by T. W. Greene in chapter 5 of *Protective Groups in Organic Synthesis*, John Wiley and Sons, New York, 1981, incorporated herein by reference in its entirety.

Acid protecting groups refer to a group which will prevent an acid group from participating in a reaction. Examples of acid protecting groups include ester derivatives of the acid group, such as methyl, methoxymethyl, methylthiomethyl, tetrahydropyranyl, methoxyethoxymethyl, benzyloxymethyl, phenylaryl, ethyl, 2,2,2-trichloroethyl, 2-methylthioethyl, t-butyl, cyclopentyl, triphenylmethyl, p-bromobenzyl and trimethylsilyl. Preferred acid-protecting groups are alkyl esters.

The salts of the above pyrroles are an additional aspect of the invention. In those instances where the compounds of the invention possess acidic functional groups various salts may be formed which are more water soluble and physiologically suitable than the parent compound. Representative pharmaceutically acceptable salts include but are not limited to the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Examples of pharmaceutically acceptable organic bases which may be used to prepare pharmaceutically acceptable salts include ammonia, amines such as triethanolamine, triethylamine, ethylamine, and the like.

When $R^6$ or $R^7$ are other than hydrogen, the compounds of formula I may exist in various isomeric forms. This invention is not related to any particular isomer but includes all possible individual isomers and racemates.

Preferred Compounds of the Invention

A preferred group of compounds of formula I are those where:

(a) $R^1$ is phenyl;
(b) $R^2$ is methyl or ethyl;
(c) $R^5$ is —$NH_2$;
(d) $R^6$ and $R^7$ are each hydrogen;
(e) X is $R^8$($C_1$–$C_6$)alkyl or phenyl substituted at the ortho position with $R^8$ where $R^8$ is —$CO_2R^{11}$; and
$R^9$ is methyl or ethyl.

Preferred substituent groups of compounds of formula (I) include the following:

(a) $R^1$ is ($C_1$–$C_4$)alkyl or phenyl;
(b) $R^1$ is phenyl substituted with one or two substituents selected from the group consisting of —($C_1$–$C_4$)alkyl, ($C_1$–$C_4$)alkoxy, phenyl($C_1$–$C_4$)alkyl, ($C_1$–$C_4$)alkylthio, halo and phenyl;
(c) R1 is phenyl substituted with one or two substituents selected from the group consisting of —($C_1$–$C_4$)alkyl, ($C_1$–$C_4$)alkoxy, ($C_1$–$C_4$)alkylthio and halo;
(d) $R^2$ is —($C_1$–$C_4$)alkyl;
(e) $R^3$ and $R^4$ are each hydrogen;
(f) $R^3$ and $R^4$ taken together are =O;
(g) $R^5$ is —$NH_2$;
(h) $R^5$ is —$NHNH_2$;
(i) $R^6$ and $R^7$ are each hydrogen;
(j) One of $R^6$ and $R^7$ is hydrogen and the other is —($C_1$–$C_4$)alkyl;
(k) One of $R^6$ and $R^7$ is hydrogen and the other is —$(CH_2)_nR^{10}$, where $R^{10}$ is —$CO_2R^{11}$, $R^{11}$ is hydrogen or —($C_1$–$C_4$)alkyl and n is 1 to 4;
(l) One of $R^6$ and $R^7$ is hydrogen and the other is —$(CH_2)_nR^{10}$, where $R^{10}$ is —$PO_3(R^{11})_2$ or —$PO_4(R^{11})_2$, $R^{11}$ is hydrogen or —($C_1$–$C_4$)alkyl and n is 1 to 4;
(m) One of $R^6$ and $R^7$ is hydrogen and the other is —$(CH_2)_nR^{10}$, where $R^{10}$ is —$SO_3R^{11}$, $R^{11}$ is hydrogen or —($C_1$–$C_4$)alkyl and n is 1 to 4;
(n) $R^6$ and $R^7$ taken together are =O;
(o) X is $R^8$($C_1$–$C_6$)alkyl where $R^8$ is —$(CH_2)_nR^{10}$, $R^{10}$ is —$CO_2R^{11}$, $R^{11}$ is hydrogen or —($C_1$–$C_4$)alkyl and n is 1 to 4;
(p) X is $R^8$($C_1$–$C_6$)alkyl where $R^8$ is —$(CH_2)_nR^{10}$, $R^{10}$ is —$PO_3(R^{11})_2$ or —$PO_4(R^{11})_2$, $R^{11}$ is hydrogen or —($C_1$–$C_4$)alkyl and n is 1 to 4;
(q) X is $R^8$($C_1$–$C_6$)alkyl where $R^8$ is —$(CH_2)_nR^{10}$, $R^{10}$ is —$SO_3R^{11}$, $R^{11}$ is hydrogen or —($C_1$–$C_4$)alkyl and n is 1 to 4;
(r) X is $R^8$($C_2$–$C_6$)alkenyl where $R^8$ is —$(CH_2)_nR^{10}$, $R^{10}$ is —$CO_2R^{11}$, $R^{11}$ is hydrogen or —($C_1$–$C_4$)alkyl and n is 1 to 4;
(s) X is $R^8$($C_2$–$C_6$)alkenyl where $R^8$ is —$(CH_2)_nR^{10}$, $R^{10}$ is —$PO_3(R^{11})_2$ or —$PO_4(R^{11})_2$, $R^{11}$ is hydrogen or —($C_1$–$C_4$)alkyl and n is 1 to 4;
(t) X is $R^8$($C_2$–$C_6$)alkenyl where $R^8$ is —$(CH_2)_nR^{10}$, $R^{10}$ is —$SO_3R^{11}$, $R^{11}$ is hydrogen or —($C_1$–$C_4$)alkyl and n is 1 to 4;
(u) X is phenyl substituted at the ortho position with $R^8$, where $R^8$ is —$(CH_2)_nR^{10}$, $R^{10}$ is —$CO_2R^{11}$, $R^{11}$ is hydrogen or ($C_1$–$C_4$)alkyl and n is 0 to 4;
(v) X is phenyl substituted at the ortho position with $R^8$, where $R^8$ is —$(CH_2)_nR^{10}$, $R^{10}$ is —$PO_3(R^{11})_2$ or $PO_4(R^{11})_2$, $R^{11}$ is hydrogen or ($C_1$–$C_4$)alkyl and n is 0 to 4;
(w) X is phenyl substituted at the ortho position with $R^8$, where $R^8$ is —$(CH_2)_nR^{10}$, $R^{10}$ is —$SO_3R^{11}$, $R^{11}$ is hydrogen or ($C_1$–$C_4$)alkyl and n is 0 to 4;
(x) X is phenyl substituted at the ortho position with —$(CH_2)_nR^{10}$ where $R^{10}$ is —$CO_2R^{11}$, $R^{11}$ is hydrogen or —($C_1$–$C_4$)alkyl and n is 0 to 4 and additionally substituted with one or two substituents selected from the group consisting of —($C_1$–$C_4$)alkyl, halo, —($C_1$–$C_4$)alkoxy or two substituents which, when taken together with the phenyl ring to which they are attached, form a naphthyl group;
(y) X is phenyl substituted at the ortho position with —$(CH_2)_nR^{10}$ where $R^{10}$ is —$PO_3(R^{11})_2$ or —$PO_4(R^{11})_2$, $R^{11}$ is hydrogen or —($C_1$–$C_4$)alkyl and n is 0 to 4 and additionally substituted with one or two substituents selected from the group consisting of —($C_1$–$C_4$)alkyl, halo, —($C_1$–$C_4$)alkoxy or two substituents which, when taken together with the phenyl ring to which they are attached, form a naphthyl group; and
(z) X is phenyl substituted at the ortho position with —$(CH_2)_nR^{10}$ where $R^{10}$ is —$SO_3R^{11}$, $R^{11}$ is hydrogen or —(C$_1$–C$_4$)alkyl and n is 0 to 4 and additionally substituted with one or two substituents selected from the group consisting of —(C$_1$–C$_4$)alkyl, halo, —(C$_1$–C$_4$)alkoxy or two substituents which, when taken together with the phenyl ring to which they are attached, form a naphthyl group.

Further typical examples of compounds of formula I which are useful in the present invention include:

2-[1-t-butyl-2-fluoro-4-(2-phosphonobenzyl)pyrrol-3-yl] glyoxamide;

2-[1-(2-methyl-6-methoxyphenyl)methyl-5-ethyl-4-(2-sulfono-5-methylbenzyl)pyrrol-3-yl]glyoxamide sodium salt;

2-[2-[1-benzyl-2-methylthio-4-(1-thioxo-6-ethoxybenzyl) pyrrol-3-yl]]acetamide;

2-[1-(3-benzyl)benzyl-2-propyl-4-(2-ethoxycarbonylbenzyl)-5-methylpyrrol-3-yl]glyoxamide;

2-[1-(4-ethylthio)benzyl-4-(2-diethoxyphosphonylbenzyl)-5-isopropylpyrrol-3-yl]acetamide;

2-[1-(3,5-difluoro)benzyl-4-(2-propoxyphosphoryl-5-methyl)benzyl)-5-methylpyrrol-3-yl]glyoxamide;

2-[1-(3-phenyl-5-ethyl)benzyl-2,5-dimethyl-4-(2-methoxysulfonyl)benzyl)pyrrol-3-yl]acetamide;

2-[1-(2-propoxy-4-fluoro)benzyl-2-ethyl-4-(2-carboxy-3,5-difluorobenzyl)-5-methylpyrrol-3-yl]acetamide calcium salt;

2-[1-(3,5-diphenyl)benzyl-2-methyl-4-(2-phosphono-naphth-1-ylmethyl)pyrrol-3-yl]glyoxamide;

2-[1-(2-(4-phenylethyl)benzyl)-2,5-di-t-butyl-4-(2-sulfono-4-fluoro)benzyl)pyrrol-3-yl]glyoxamide;

2-[1-benzyl-2-butyl-4-(2-phosphoro-6-ethylbenzyl)pyrrol-3-yl]acetamide magnesium salt lithium salt;

2-[1-(4-ethoxy)benzyl-4-(2-methoxycarbonylbenzyl)pyrrol-3-yl]glyoxamide;

2-[1-(5-phenylpropyl)benzyl-2-ethyl-4-(2-dipropoxyphosphonylphenylmethyl)-5-ethylpyrrol-3-yl] acetamide;

2-[1-(3,5-dimethylthio)phenylmethyl-4-(2-methoxysulfonylphenylmethyl)pyrrol-3-yl]glyoxamide;

2-[1-(2-methyl-6-methoxy)benzyl-5-ethyl-4-(3-phosphono-2-methylprop-1-yl)pyrrol-3-yl]glyoxamide;

2-[1-benzyl-2-methylthio-4-(1-phosphoro-6-sulfono-4-hexen-1-yl)pyrrol-3-yl]acetamide sodium salt;

2-[1-(3-benzyl)benzyl-2-propyl-4-(1-ethoxycarbonyl-5-methoxyphosphorylpent-1-yl)-5-methylpyrrol-3-yl] glyoxamide;

2-[1-(4-ethylthio)benzyl-4-(1-thioxo-3-diethoxyphosphonylprop-1-yl)-5-isopropylpyrrol-3-yl]-1-thioxoacetamide;

2-[1-(3,5-difluoro)benzyl-4-(2-ethyl-4-propoxyphosphorylbut-1-yl)-5-methylpyrrol-3-yl] glyoxamide;

2-[1-(3-phenyl-5-ethyl)benzyl-2,5-dimethyl-4-(1-methoxyphosphonyl-7-methoxysulfonyl-4-hepten-1-yl) benzyl)pyrrol-3-yl]acetamide;

2-[1-(2-propoxy-4-fluoro)benzyl-2-ethyl-4-(1-butyl-4-carboxybut-1-yl)-5-methylpyrrol-3-yl]acetamide;

2-[1-(3,5-diphenyl)benzyl-2-methyl-4-(1,5-diphosphonopent-1-yl)pyrrol-3-yl]glyoxamide potassium salt;

2-[1-(4-phenylethyl)benzyl-2,5-di-t-butyl-4-(1-isopropyl-6-sulfonohex-1-yl)benzyl)pyrrol-3-yl]glyoxamide;

2-[2-[1-benzyl-2-butyl-4-(1-ethyl-4-phosphoro-3-buten-1-yl)pyrrol-3-yl]]acetamide magnesium salt;

2-[1-(4-ethoxy)benzyl-4-(1,5-dimethoxycarbonylpent-1-yl) pyrrol-3-yl]glyoxamide;

2-[1-(5-phenylpropyl)benzyl-2-ethyl-4-(1-thioxo-7-dipropoxyphosphonyl-4-hepten-1-yl)-5-ethylpyrrol-3-yl] acetamide;

2-[1-(3,5-dimethylthio)benzyl-4-(1-methyl-3-methoxysulfonylprop-1yl)pyrrol-3-yl]glyoxamide;

Synthesis Methods

Compounds of formula I where $R^5$ is —NH$_2$ can be prepared as shown in Scheme I, below.

2-[1-t-butyl-2-fluoro-4-(1,4-dicarboxybut-1-yl)pyrrol-3-yl] glyoxamide;

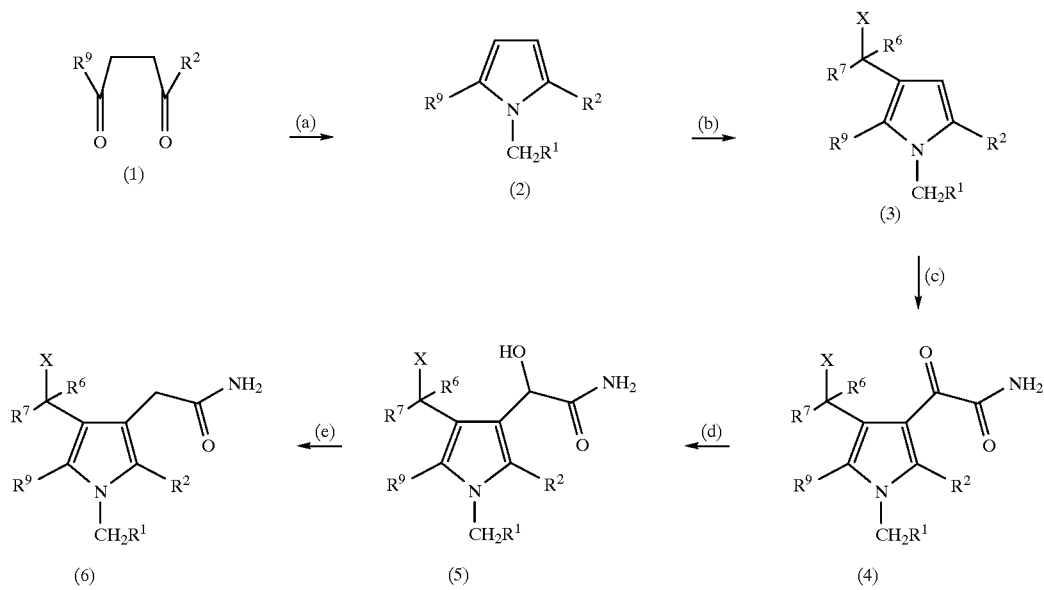

Scheme I

An appropriately substituted gamma-diketone (1) is reacted with an alkylamine of the formula NHCH$_2$R$^1$ to give pyrrole (2). Under Friedel-Crafts conditions, using a suitable Lewis-acid catalyst such as stannic chloride, aluminum chloride, or titanium tetrachloride (preferably stannic chloride) pyrrole (2) is ring alkylated with an alkyl or arylalkyl halide compound of the formula $ZCR^6R^7X$ where Z is a suitable halogen and $R^8$ of X is a protected acid or ester. The reaction is preferably conducted in a halogenated hydrocarbon solvent, such as dichloromethane, at ambient temperatures and allowed to proceed for from about 1 to about 24 hours.

Intermediate (3) is converted to (4) by sequential treatment with oxalyl chloride followed by ammonia. Selective reduction of (4) is accomplished in a two step process. In a hydride reduction using, for example, sodium borohydride, the hydroxy intermediate (5) is prepared which can be further reduced using either catalytic or hydride reduction (preferably palladium on carbon) to prepare (6). Deprotection of $R^8$ to the acid may be readily achieved by conventional techniques. For example, when an alkyl ester is used as a protecting group, deprotection can be accomplished by treatment with a base, such as sodium hydroxide.

In an alternate procedure, compounds of formula I may be prepared according to Scheme II.

Hydride reduction of (7), using trifluoroacetic acid and triethylsilane at elevated temperatures, achieves compound (3) where $R^6$ and $R^7$ are hydrogen. Alternately, compounds where $R^6$ and $R^7$ are hydrogen may be prepared by converting the carbonyl of (7) to sulfur by treatment with Lawesson's reagent, and then reducing the sulfur using Raney nickel catalyst.

Compounds of formula I where $R^6$ and $R^7$ are —$(C_1$–$C_4)$ alkyl can be accomplished by converting the reactive acyl function of (7), to the appropriate alkyl substituent as described by J. Pataki, et al., J. Org. Chem., 47, 1133 (1982) using $ZnMe_2$ or by the method of C. V. Kim, et al., Tet. Lett., 35(19), 3017 (1994), using $AlMe_3$. Alternately, the method of M. T. Reez, et al., J. Org. Chem., 48, 254 (1983) using $ZnMe_2$ and RLi where R is $(C_1$–$C_4)$alkyl may be employed to prepare compound (8).

Compounds where $R^6$ or $R^7$ are $(CH_2)_nR^{10}$ where $R^{10}$ is an acid or an ester can be prepared by treating the carbonyl of intermediate (7) with an appropriate Wittig reagent followed by catalytic reduction of the double bond.

Conversion of intermediate (3) to (8) is then achieved as described in Scheme I, step (c) above, using oxalyl chloride followed by ammonia.

Hydride reduction of (8) using sodium borohydride, affords intermediate (9). Further reduction of (9) can be

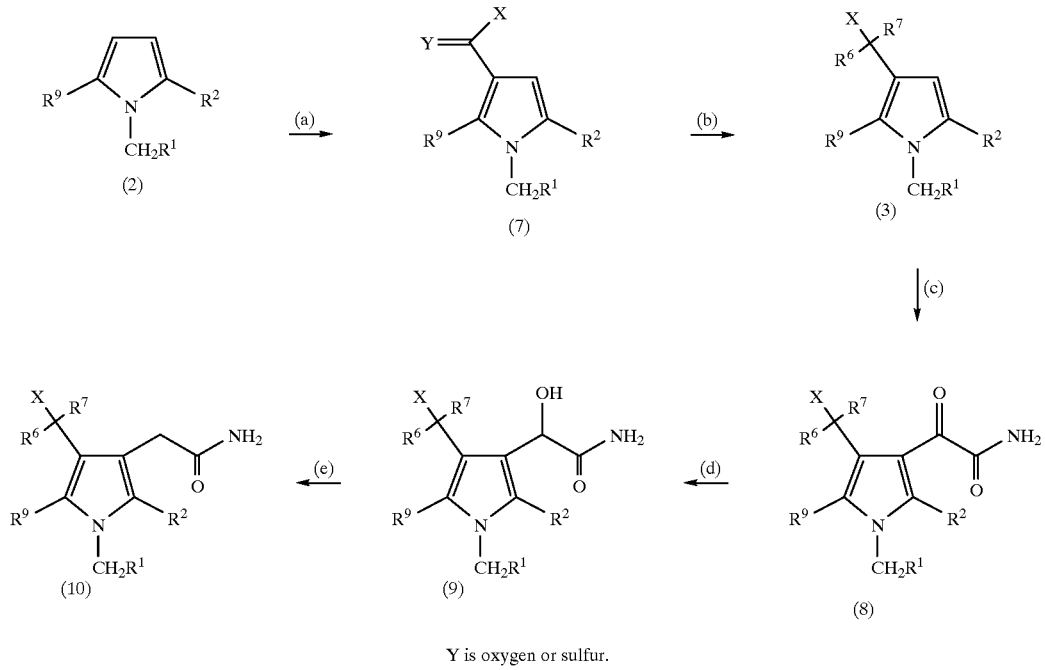

Scheme II

Y is oxygen or sulfur.

Under Friedel-Crafts conditions in the presence of a Lewis acid, as described above, compound (2) is acylated using a cyclic anhydride, such as succinic anhydride or an acid chloride compound of the formula

where Z is a halogen and the acid function, $R^8$, of X is protected with an acid protecting group, such as an alkyl group.

accomplished either by hydrogenolysis using hydrogen and palladium on carbon or with trifluoroacetic acid and triethyl silane. The protected acid functionalities of (10) can then be deprotected as described above.

Compounds of formula I where $R^5$ is —$NHNH_2$ can be prepared as shown in Scheme III on the following page.

Scheme III

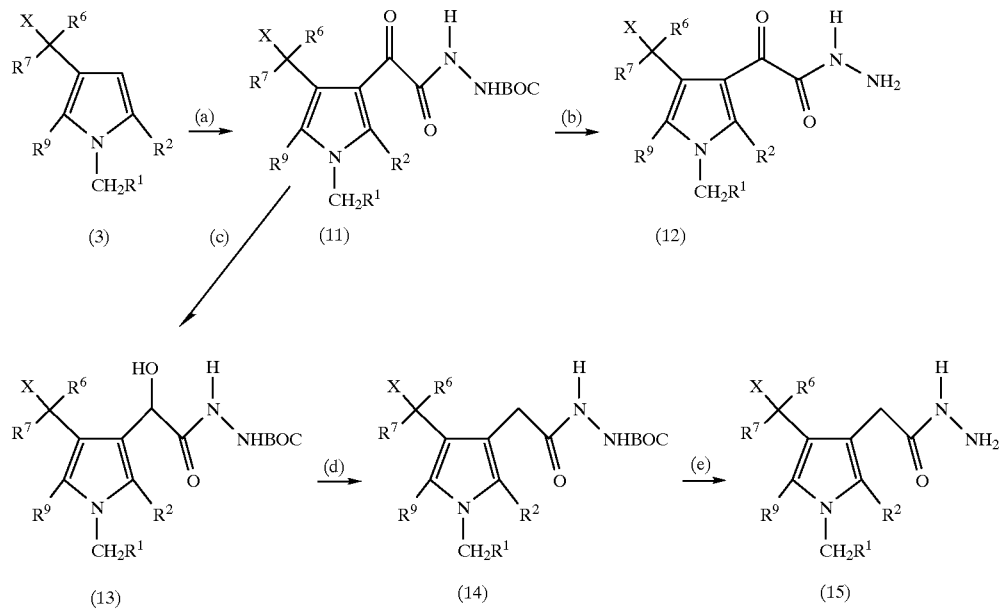

Pyrrole (3) is treated first with oxalyl chloride and then with a protected hydrazide, such as tert-butylcarbazate, to give (11) which may be hydrolyzed using an aqueous base, preferably sodium hydroxide, to yield (12).

Stepwise reduction of (11) using, for example, sodium borohydride and then hydrogen in the presence of pallidium on carbon gives (14) which may be hydrolyzed using an aqueous base to provide (15).

The intermediates and final products may be isolated and purified by conventional techniques, for example by concentration of the solvents, followed by washing of the residue with water, then purification by conventional techniques such as chromatography or recrystallization.

It will be readily appreciated by the skilled artisan that the starting materials are either commercially available or can be readily prepared by known techniques from commercially available starting materials.

When $R^6$ or $R^7$ are other than hydrogen, the present invention may have one stereo center. The methods, formulations and compounds of the present invention encompass the diastereomers and racemates and their individual stereo isomers. Diastereomeric pairs may be obtained according to procedures well known in the art, for example, by formation of a diastereomeric salt.

The following examples further illustrate the preparation of the compounds of this invention. The examples are illustrative only and are not intended to limit the scope of the invention in any way.

EXAMPLE 1

2-[1-benzyl-2,5-dimethyl-4-(2-carboxyphenylmethyl)pyrrol-3-yl]glyoxamide

Part A. Preparation of 1-benzyl-2,5-dimethyl-4-(2-methoxycarbonylbenzyl)pyrrol

To a solution of 925 mg. (5.0 mmol) of 1-benzyl-2,5-dimethylpyrrole [E. Wolthuis et al., J. Org. Chem., 30, 190, (1965)] and 1.3 gm. (5.5 mmol) of methyl 2-bromomethyltoluate in 100 ml. of dichloromethane was added 10 ml. of a 1M solution of stannic chloride in dichloromethane. After stirring for 22.5 hours, the solution was washed with cold, aqueous ammonia, washed with brine, dried over sodium sulfate, and evaporated in vacuo. The residue was chromatographed on silica gel eluting with a gradient hexane/5–15% ether to give (3) ($R^9$=$R^2$=Me, $R^1$=Ph, $R^6$=$R^7$=H, X=2—MeO$_2$CPh), 650 mg., 42%, amorphous solid.

Analyses for $C_{24}H_{24}N2O_4$: Calculated: C 71.27; H 5.98; N 6.93 Found: C 71.54; H 5.97; N 6.76

Part B. Preparation of 2-[1-benzyl-2,5-dimethyl-4-(2-carboxybenzyl)pyrrol-3-yl]glyoxamide.

A solution of 650 mg. of the compound of Part A in 75 ml. of dichloromethane was cooled in an ice-water bath. After adding 0.2 ml. of oxalyl chloride, the cooling bath was removed and the solution was stirred for 40 minutes, cooled in ice-water, and saturated with ammonia. The suspension was washed with water, washed with brine, dried over sodium sulfate, and evaporated in vacuo. An ethyl acetate solution of the residue was filtered through silica gel to give (4) ($R^2$=$R^9$=Me, $R^1$=Ph, $R^6$=$R^7$=H, X=2-HO$_2$CPh), 800 mg., 100% as an amorphous solid which was dissolved in 75 ml. of ethanol containing 5 ml. of 2N sodium hydroxide and stirred for 22 hours. The solution was acidified with 5N hydrochloric acid and extracted with ethyl acetate. The organic phase was washed with brine, dried over sodium sulfate, and evaporated in vacuo. The residue was crystallized from ethyl acetate to yield title compound, 375 mg., 49%, melting at 194–195° C. with decomposition.

Analyses for $C_{23}H_{22}N_2O_4$: Calculated: C 70.75; H 5.66; N 7.17 Found: C 70.71; H 5.58; N 6.92

EXAMPLE 2

1-benzyl-2,5-dimethyl-4-(2-carboxybenzyl)pyrrole-3-acetamide

Part A. Preparation of 1-benzyl-2,5-dimethyl-4-(2-methoxycarbonylbenzyl)pyrrole-3-acetamide.

A solution of 585 mg. of (4) ($R^2$=$R^9$=Me, $R^1$=Ph, $R^6$=$R^7$=H, X=2-MeO$_2$CPh) in 50 ml. of methanol and 10 ml. of tetrahydrofuran was treated with 0.3 gm. of sodium borohydride for 1 hour, diluted with water, and extracted with ethyl acetate. The organic phase was washed with brine, dried over sodium sulfate, and evaporated in vacuo to give (5) ($R^2=R^9=Me$, $R^1=Ph$, $R^6=R^7=H$, X=2-$MeO_2CPh$) which was dissolved in 75 ml. of ethanol containing 0.2 ml. of trifluoroacetic acid and stirred under 1 atmosphere of hydrogen in the presence of 0.3 gm. of 10% Pd/C for 9 hours, filtered, and evaporated in vacuo. An ethyl acetate solution of the residue was filtered through silica gel to give (6) ($R^2=R^9=Me$, $R^1=Ph$, $R^6=R^7=H$, X=2-$MeO_2CPh$), 215 mg., 38% (two steps), mp 134–137° C. ether/hexane.

Analyses for $C_{24}H_{26}N_2O_3$: Calculated: C 73.82; H 6.71; N 7.17 Found: C 73.52; H 6.92; N 6.98

Part B. Preparation of 1-benzyl-2,5-dimethyl-4-(2-carboxybenzyl)pyrrole-3-acetamide.

A solution of 195 mg. of the compound of Part A in 25 ml. of ethanol and 2 ml. of 2N sodium hydroxide was stirred for 16 hours, acidified with 5N hydrochloric acid, and extracted with ethyl acetate. The organic phase was washed with brine, dried over sodium sulfate, and evaporated in vacuo. The residue crystallized from ether to give title compound, 95 mg., 50%, mp 153–157° C. with decomposition.

Analyses for $C_{23}H_{24}N_2O_3$: Calculated: C 73.38; H 6.43; N 7.28 Found: C 72.71; H 6.44; N 7.28

EXAMPLE 3

1-benzyl-2,5-dimethyl-4-(2-methoxycarbonylbenzyl) pyrrole-3-glyoxhydrazide

A solution of 545 mg. (1.7 mmol) of the compound of Example 1A in 75 ml. of dichloromethane was cooled in ice-water and treated with 0.18 ml. (2.0 mmol) of oxalyl chloride for 10 minutes followed by the addition of 235 mg. (2.0 mmol) of t-butylcarbazate and an additional 30 minutes of stirring. The solution was washed with water, washed with brine, dried over sodium sulfate, and evaporated in vacuo. The residue was chromatographed on silica gel eluting with a gradient hexane/25–100% ether to give (11) ($R^2=R^9=Me$, $R^1=Ph$, X=2-$MeO_2Ph$), 300 mg., 35%, which was dissolved in 50 ml. of ethanol containing 6 ml. of 5N sodium hydroxide and stirred 23 hours. The pH was adjusted to 6–7 with 5N hydrochloric acid and the solution was extracted with ethyl acetate. The organic phase was washed with brine, dried over sodium sulfate, and evaporated in vacuo to yield title compound as an amorphous solid, 245 mg., 100%.

Analyses for $C_{23}H_{23}N_3O_4$: Calculated: C 68.14; H 5.72; N 10.36 Found: C 60.90; H 6.45; N 7.57

EXAMPLE 4

2-[1-benzyl-2,5-dimethyl-4-(4-carboxybut-1-yl) pyrrol-3-yl]glyoxamide

Part A. Preparation of methyl [1-benzyl-2,5-dimethyl-4-(4-carboxybut-1-yl)pyrrol-3-yl]glyoxamide A solution of 1.85 gm. (10 mmol) of (2) ($R^2=R^9=Me$, $R^1=Ph$) and 1.5 ml. (12 mmol) of methyl 3-chloroformylpropionate in 150 ml. of dichloromethane was treated with 20 ml. of 1.0 M stannic chloride in dichloromethane for 1 hour, washed with water, washed with brine, dried over sodium sulfate, and evaporated in vacuo. The residue was chromatographed on silica gel eluting with a gradient hexane/25–40% ether to give (7) ($R^2=R^9=Me$, $R^1=Ph$, X=$(CH_2)_2CO_2Me$, $R^6$ & $R^7$=O), 1.18 gm., 40%, as an oil which was dissolved in 100 ml. of tetrahydrofuran and stirred with 1.8 gm. of Lawesson's reagent for 3 hours, diluted with ethyl acetate, washed with brine, dried over sodium sulfate, and evaporated in vacuo. The residue was chromatographed on silica gel eluting with a gradient hexane/20–35% ether to give (7) ($R^2=R^9=Me$, $R^1=Ph$, X=$(CH_2)_2CO_2Me$, $R^6$ & $R^7$=S), 930 mg., 75%, which was stirred in 100 ml. of methanol and ca. 5 gm. of Raney nickel catalyst for 40 minutes. The solution was decanted and evaporated in vacuo. The residue was chromatographed on silica gel eluting with a gradient hexane/10–15% ether to give (3) ($R^2=R^9=Me$, $R^1=Ph$, X=$(CH_2)_2CO_2Me$), 480 mg, 57%, as an oil which was dissolved in 70 ml. of dichloromethane, cooled at −5° C., treated with 0.18 ml. of oxalyl chloride for 10 minutes, saturated with ammonia gas, washed with water, washed with brine, dried over sodium sulfate, and evaporated in vacuo. The residue was chromatographed on silica gel eluting with ether to give (8) ($R^1=Ph$, $R^2=R^9=Me$, $R^6=R^7=H$, X=$(CH_2)_2CO_2Me$), 415 mg., 75%, mp 123–125° C./$Et_2O$.

Analyses for $C_{20}H_{24}N_2O_4$: Calculated: C 67.40; H 6.79; N 7.86 Found: C 67.76; H 6.87; N 7.86

Part B. Preparation of [1-benzyl-2,5-dimethyl-4-(4-carboxybut-1-yl)pyrrol-3-yl]glyoxamide A solution of 400 mg. of the compound of Part A and 10 ml. of 2.0N sodium hydroxide in 60 ml. of ethanol was stirred for 18.5 hours, acidified with hydrochloric acid, and extracted with ethyl acetate. The organic phase was washed with brine, dried over sodium sulfate, and evaporated in vacuo to give title compound as an amorphous solid.

Analyses for $C19H_{22}N_2O_4$: Calculated: C 66.65; H 6.48; N 8.18 Found: C 66.92; H 6.67; N 6.06

Therapeutic Use of Pyrroles

The pyrrole compounds described herein are believed to achieve their beneficial therapeutic action principally by direct inhibition of human $sPLA_2$, and not by acting as antagonists for arachidonic acid, nor other active agents below arachidonic acid in the arachidonic acid cascade, such as 5-lipoxygenases, cyclooxygenases, etc.

The method of the invention for inhibiting $sPLA_2$ mediated release of fatty acids comprises contacting $sPLA_2$ with an therapeutically effective amount of the compound of formula (I), or salts thereof.

The compounds of the invention may be used in a method of treating a mammal (e.g., a human) to alleviate the pathological effects of septic shock, adult respiratory distress syndrome, pancreatitis, trauma, bronchial asthma, allergic rhinitis, and rheumatoid arthritis; wherein the method comprises administering to the mammal a compound of formula (I) in a therapeutically effective amount. A "therapeutically effective" amount is an amount sufficient to inhibit $sPLA_2$ mediated release of fatty acid and to thereby inhibit or prevent the arachidonic acid cascade and its deleterious products. The therapeutic amount of compound of the invention needed to inhibit $sPLA_2$ may be readily determined by taking a sample of body fluid and assaying it for $sPLA_2$ content by conventional methods.

Pharmaceutical Formulations of the Invention

As previously noted the compounds of this invention are useful for inhibiting $sPLA_2$ mediated release of fatty acids such as arachidonic acid. By the term, "inhibiting" is meant the prevention or therapeutically significant reduction in release of $sPLA_2$ initiated fatty acids by the compounds of the invention. By "pharmaceutically acceptable" it is meant the carrier, diluent or excipient must be compatible with the other ingredients of the formulation and not deleterious to the recipient thereof.

In general, the compounds of the invention are most desirably administered at a concentration that will generally afford effective results without causing any serious side effects and can be administered either as a single unit dose, or if desired, the dosage may be divided into convenient subunits administered at suitable times throughout the day.

The specific dose of a compound administered according to this invention to obtain therapeutic or prophylactic effects will, of course, be determined by the particular circumstances surrounding the case, including, for example, the route of administration, the age, weight and response of the individual patient, the condition being treated and the severity of the patient's symptoms. Typical daily doses will contain a non-toxic dosage level of from about 0.01 mg/kg to about 50 mg/kg of body weight of an active compound of this invention.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

A "chronic" condition means a deteriorating condition of slow progress and long continuance. As such, it is treated when it is diagnosed and continued throughout the course of the disease. An "acute" condition is an exacerbation of short course followed by a period of remission. In an acute event, compound is administered at the onset of symptoms and discontinued when the symptoms disappear.

Pancreatitis, trauma-induced shock, bronchial asthma, allergic rhinitis and rheumatoid arthritis may occur as an acute event or a chronic event. Thus, the treatment of these conditions contemplates both acute and chronic forms. Septic shock and adult respiratory distress syndrome, on the other hand, are acute conditions treated when diagnosed.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the pyrrole compounds of the invention together with a pharmaceutically acceptable carrier or diluent therefor. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound according to Formula (I) or a pharmaceutically acceptable salt, solvate, or prodrug thereof.

Formulation 1

Hard gelatin capsules are prepared using the following ingredients:

|  | Quantity (mg/capsule) |
| --- | --- |
| 2-[1-(4-phenylethyl)benzyl-2,5-di-t-butyl-4-(2-sulfono-4-fluoro)benzyl)pyrrol-3-yl]glyoxamide sodium salt | 250 |
| Starch, dried | 200 |
| Magnesium stearate | 10 |
| Total | 460 mg |

Formulation 2

A tablet is prepared using the ingredients below:

|  | Quantity (mg/tablet) |
|---|---|
| 2-[1-(3,5-difluoro)benzyl-4-(2-propoxyphosphoryl-5-methyl)benzyl)-5-methylpyrrol-3-yl]glyoxamide | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
|---|---|
| 2-[1-benzyl-2-butyl-4-(2-phosphoro-6-ethylbenzyl)pyrrol-3-yl]acetamide magnesium salt | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | |
|---|---|
| 2-[1-(315-dimethylthio)benzyl-4-(2-methoxysulfonylbenzyl)pyrrol-3-yl]glyoxamide | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| 2-[1-(3-benzyl)benzyl-2-propyl-4-(2-ethoxycarbonyl-5-methoxyphosphorylpent-1-yl)-5-methylpyrrol-3-yl]glyoxamide | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| 2-[1-(3-phenyl-5-ethyl)benzyl-2,5-dimethyl-4-(2-methoxyphosphonyl-7-methoxysulfonyl-4-hepten-1-yl)benzyl)pyrrol-3-yl]acetamide | 225 mg |
| Saturated fatty acid glyceride | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| 2-[1-benzyl-2-butyl-4-(2-ethyl-4-phosphoro-3-buten-1-yl)pyrrol-3-yl]-1-thioxoacetamide | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | | |
|---|---|---|
| 2-[1-(3,5-dimethylthio)benzyl-4-(2-methyl-3-methoxysulfonylprop-lyl)pyrrol-3-yl]glyoxamide | 100 | mg |
| Isotonic saline | 1,000 | ml |

The solution of the above ingredients generally is administered intravenously to a subject at a rate of 1 ml per minute.

Assay Experiments

Assay Example 1

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A. Dennis, *Analytical Biochemistry*, 204, pp. 190–197, 1992 (the disclosure of which is incorporated herein by reference):

Reagents:

| REACTION BUFFER | |
|---|---|
| $CaCl_2.2H_2O$ | (1.47 g/L) |
| KCl | (7.455 g/L) |
| Bovine Serum Albumin (fatty acid free) | (1 g/L) |
| (Sigma A-7030, product of Sigma Chemical Co. St. Louis MO, USA) | |
| TRIS HCl | (3.94 g/L) |
| pH 7.5 (adjust with NaOH) | |
| ENZYME BUFFER | |
| 0.05 $NaOAc.3H_2O$; pH 4.5 | |
| 0.2 NaCl | |
| Adjust pH to 4.5 with acetic acid | |
| DTNB—5,5'-dithiobis-2-nitrobenzoic acid | |
| RACEMIC DIHEPTANOYL THIO—PC | |
| racemic 1,2-bis(heptanoylthio)-1,2-dideoxy-sn-glycero-3-phosphorylcholine | |
| TRITON X100 ™ prepare at 6.249 mg/ml in reaction buffer to equal 10 uM. | |
| TRITON X100 ™ is a polyoxyethylene non-ionic detergent supplied by | |
| Pierce Chemical Company | |
| 3747 N. Meridian Road | |
| Rockford, Illinois 61101 | |
| REACTION MIXTURE | |

A measured volume of racemic diheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:
1. Add 0.2 ml reaction mixture to all wells;
2. Add 10 ul test compound (or solvent blank) to appropriate wells, mix 20 seconds;
3. Add 50 nanograms of $sPLA_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ were determined by plotting log concentration versus inhibition values in the range from 10–90% inhibition.

Compounds of the instant invention were tested in Assay Example 1 and were found to be effective.

Assay Example 2

Method:

Male Hartley strain guinea pigs (500–700 g) were killed by cervical dislocation and their heart and lungs removed intact and placed in aerated (95% $O_2$:5% $CO_2$) Krebs buffer. Dorsal pleural strips (4×1×25 mm) were dissected from intact parenchymal segments (8×4×25 mm) cut parallel to the outer edge of the lower lung lobes. Two adjacent pleural strips, obtained from a single lobe and representing a single tissue sample, were tied at either end and independently attached to a metal support rod. One rod was attached to a Grass force-displacement transducer Model FTO3C, product of Grass Medical Instruments Co., Quincy, Mass., USA). Changes in isometric tension were displayed on a monitor and thermal recorder (product of Modular Instruments, Malvern, Pa.). All tissues were placed in 10 ml jacketed tissue baths maintained at 37° C. The tissue baths were continuously aerated and contained a modified Krebs solution of the following composition (millimolar) NaCl, 118.2; KCl, 4.6; $CaCl_2.2H_2O$, 2.5; $MgSO_4.7H_2O$, 1.2; $NaHCO_3$, 24.8; $KH_2PO_4$, 1.0; and dextrose, 10.0. Pleural strips from the opposite lobes of the lung were used for paired experiments. Preliminary data generated from tension/response curves demonstrated that resting tension of 800 mg was optimal. The tissues were allowed to equilibrate for 45 min. as the bath fluid was changed periodically.

Cumulative Concentration-Response Curves:

Initially tissues were challenged 3 times with KCl (40 mM) to test tissue viability and to obtain a consistent response. After recording the maximal response to KCl, the tissues were washed and allowed to return to baseline before the next challenge. Cumulative concentration-response curves were obtained from pleural strips by increasing the agonist concentration ($sPLA_2$) in the tissue bath by half-$log_{10}$ increments while the previous concentration remained in contact with the tissues (Ref.1, supra.). Agonist concentration was increased after reaching the plateau of the contraction elicited by the preceding concentration. One concentration-response curve was obtained from each tissue.

To minimize variability between tissues obtained from different animals, contractile responses were expressed as a percentage of the maximal response obtained with the final KCl challenge. When studying the effects of various drugs on the contractile effects of sPLA$_2$, the compounds and their respective vehicles were added to the tissues 30 minutes prior to starting the sPLA$_2$ concentration-response curves.

Statistical Analysis:

Data from different experiments were pooled and presented as a percentage of the maximal KCl responses (mean±S.E.). To estimate the drug induced rightward shifts in the concentration response curves, the curves were analyzed simultaneously using statistical nonlinear modeling methods similar to those described by Waud (1976), Equation 26, p. 163, (Ref.2). The model includes four parameters: the maximum tissue response which was assumed the same for each curve, the ED$_{50}$ for the control curve, the steepness of the curves, and the pA$_2$, the concentration of antagonist that requires a two-fold increase in agonist to achieve an equivalent response. The Schild slope was determined to be 1, using statistical nonlinear modeling methods similar to those described by Waud (1976), Equation 27, p. 164 (Ref. 2). The Schild slope equal to 1 indicates the model is consistent with the assumptions of a competitive antagonist; therefore, the pA$_2$ may be interpreted as the apparent K$_B$, the dissociation constant of the inhibitor.

To estimate the drug-induced suppression of the maximal responses, sPLA$_2$ responses (10 ug/ml) were determined in the absence and presence of drug, and percent suppression was calculated for each pair of tissues.

Ref. 1—van, J. M.: Cumulative dose-response curves. II. Technique for the making of dose-response curves in isolated organs and the evaluation of drug parameters. *Arch. Int. Pharmacodyn. Ther.,* 143: 299–330, 1963.

Ref. 2—Waud, D.: Analysis of dose-response relationships. in *Advances in General and Cellular Pharmacology* eds Narahashi, Bianchi 1:145–178, 1976.

Compounds of the instant invention were tested in Assay Example 2 and were found to be effective.

We claim:

1. A compound of formula I

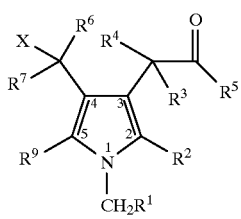

(I)

wherein

R$^1$ is hydrogen, (C$_1$–C$_4$)alkyl, phenyl or phenyl substituted with one or two (C$_1$–C$_4$)alkyl, (C$_1$–C$_4$)alkoxy, phenyl (C$_1$–C$_4$)alkyl, (C$_1$–C$_4$)alkylthio, halo or phenyl substituents;

R$^2$ is hydrogen, (C$_1$–C$_4$)alkyl, halo, (C$_1$–C$_4$)alkoxy or (C$_1$–C$_4$)alkylthio;

R$^3$ and R$^4$ are hydrogen or taken together are =O;

R$^5$ is —NH$_2$ or —NHNH$_2$;

R$^6$ and R$^7$ are each hydrogen; or one of R$^6$ and R$^7$ is hydrogen, and the other is (C$_1$–C$_4$)alkyl or —(CH$_2$)$_n$R$^{10}$; or R$^6$ and R$^7$ taken together are =O or =S;

X is R$^8$(C$_1$–C$_6$)alkyl, R$^8$(C$_2$–C$_6$)alkenyl, or phenyl substituted at the ortho position with R$^8$ and additionally optionally substituted with one or two (C$_1$–C$_4$)alkyl, halo, or (C$_1$–C$_4$)alkoxy substituents, or with two substituents that together with the phenyl ring form a naphthyl group;

R$^8$ is (CH$_2$)$_n$R$^{10}$;

R$^9$ is hydrogen, methyl or ethyl;

R$^{10}$ is —CO$_2$R$^{11}$, —PO$_3$(R$^{11}$)$_2$, —PO$_4$(R$^{11}$)$_2$ or —SO$_3$R$^{11}$;

R$^{11}$ is hydrogen or (C$_1$–C$_4$)alkyl; and n is 0 to 4;

or a pharmaceutically acceptable salt thereof.

2. A compound of formula I

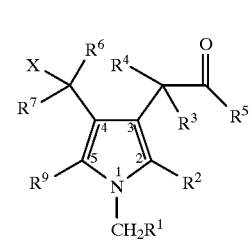

(I)

wherein

R$^1$ is phenyl;

R$^2$ and R$^9$, independently, are methyl or ethyl;

R$^3$ and R$^4$ are hydrogen or taken together are =O;

R$^5$ is —NH$_2$;

R$^6$ and R$^7$ are hydrogen;

X is R$^8$(C$_1$–C$_6$)alkyl or phenyl substituted at the ortho position with R$^8$;

R$^8$ is —CO$_2$R$^{11}$; and

R$^{11}$ is hydrogen or (C$_1$–C$_4$)alkyl;

or a pharmaceutically acceptable salt thereof.

3. The compound of claim 2 which is 2-[1-benzyl-2,5-dimethyl-4-(2-carboxyphenylmethyl)pyrrol-3-yl]glyoxamide.

4. A pharmaceutical formulation comprising a compound of claim 1 together with a pharmaceutically acceptable carrier or diluent therefor.

5. A pharmaceutical formulation comprising a compound of claim 2 and a pharmaceutically acceptable carrier or diluent.

6. A method of treating a condition caused by sPLA$_2$-mediated release of fatty acids in a mammal comprising administering to the mammal an amount effective of a compound of claim 1 that inhibits that release.

7. A method of claim 6 wherein the mammal is a human.

8. A method of claim 6 wherein the compound is 2-[1-benzyl-2,5-dimethyl-4-(2-carboxyphenylmethyl)pyrrol-3-yl]glyoxamide.

9. A method of alleviating the pathological effects of a human condition selected from septic shock, adult respiratory distress syndrome, pancreatitis, trauma-induced shock, bronchial asthma, allergic rhinitis, and rheumatoid arthritis which comprises administering a therapeutically effective amount of a compound of claim 1 to a human suffering from the condition.

10. A method of claim 9 wherein the compound is 2-[1-benzyl-2,5-dimethyl-4-(2-carboxyphenylmethyl)pyrrol-3-yl]glyoxamide.

* * * * *